United States Patent [19]

Fischer et al.

[11] Patent Number: 4,874,889
[45] Date of Patent: Oct. 17, 1989

[54] ISOMERIZATION OF 2-PENTENOATES TO 3-PENTENOATES

[75] Inventors: Rolf Fischer, Heidelberg; Franz Merger, Frankenthal; Hans-Juergen Gosch, Bad Duerkheim, all of Fed. Rep. of Germany

[73] Assignee: BASF Aktiengesellschaft, Ludwigshafen, Fed. Rep. of Germany

[21] Appl. No.: 122,941

[22] Filed: Nov. 18, 1987

[30] Foreign Application Priority Data

Nov. 27, 1986 [DE] Fed. Rep. of Germany ....... 3640597

[51] Int. Cl.$^4$ ............................................. C07C 67/333
[52] U.S. Cl. ..................... 560/205; 560/220; 560/221; 562/598
[58] Field of Search ............... 560/220, 221, 205, 130, 560/139; 562/598

[56] References Cited

U.S. PATENT DOCUMENTS 4,327,225 4/1982 Isogai et al. .......................... 560/205
4,529,815 7/1985 Schneider et al. .................. 560/205

OTHER PUBLICATIONS

Patent Abstracts of Japan, vol. 2, No. 34, Mar. 8, 1978.
Journal of Organic Chemistry, vol. 47, No. 14, Jul. 2, 1982, American Chemical Society, pp. 2745–2748, J. Hine et al: "Double Bond Stabilizing . . . ".
Chemical Abstracts, vol. 69, No. 11, Sep. 9, 1968, p. 4041, Col. 2, Abstract No. 43226v.
Tetrahedron Letters, vol. 25, No. 45, 1984, Pergamon Press Ltd., pp. 5181–5182, Idea et al: A Practical Synthesis . . .
Patent Abstracts of Japan, vol. 6, No. 7 (C-87) (885), Jan. 16, 1982.
Helvetica Chimica Acta, vol. 64, No. 94, 1981, Swiss Chemical Association, pp. 1023–1025, Kreb: A Note on Stereochemical . . .
The Journal of Organic Chemistry, vol. 33, Mar. 12, 1988, pp. 1671–1673.
Helv. Chimica Acta, vol. 64, (1981), pp. 1023–1025.
Tetrahedron Letters, vol. 25, No. 40, p. 5181 (1984).
Canadian Journal of Chemistry, vol. 46, No. 13, Jul. 1, 1968, pp. 2225–2232.
The Journal of Org. Chemistry, vol. 47, 1982, pp. 2745–2748.
Japan Patent Publication 55345/1981.

*Primary Examiner*—Werren B. Lone
*Attorney, Agent, or Firm*—Oblon, Spivak, McClelland, Maier & Neustadt

[57] ABSTRACT

3-Pentenoates are prepared by isomerization of 2-pentenoates to 3-pentenoates by a process in which the 2-pentenoate is treaated with from 0.01 to 0.5 mole of cyclic tertiary amine having a p$K_a$ of >6 per mole of 2-pentenoate at from 50° to 250° C. and the 3-pentenoate is distilled off continuously.

5 Claims, No Drawings

ISOMERIZATION OF 2-PENTENOATES TO 3-PENTENOATES

J. Org. Chem. 33 (1968), 1671 et seq. discloses that 2-pentenoates can be isomerized photochemically to 3-pentenoates. A disadvantage of this procedure is that it requires a very long irradiation time in order to achieve adequate yields. Furthermore, it is necessary to use very dilute 2-pentenoate solutions, which are expensive to work up.

It is also known that 2-pentenoates can be converted to 3-pentenoates by means of organometallic bases, such as lithium diisopropylamide (Helv. Chim. Acta 64 (1981), 1023 et seq.) and potassium disilazide (Tetrahedron Lett. 25 (1984), 5181). A particular disadvantage, however, is that the organometallic bases are very sensitive to water, necessitating a very careful procedure under a protective gas atmosphere. Moreover, these bases have to be used at very low temperatures, which is technically very complicated.

According to Can. J. Chem. 46 (1968), 2225 et seq., 2-pentenoates can be converted to 3-pentenoates by a purely thermal method at above 250° C. However, this requires considerable reaction times, for example more than 150 hours, in order to achieve an adequate conversion.

J. Org. Chem. 47 (1982), 2745–2748 furthermore describes the isomerization of pentenoates with equimolar amounts of 1,8-diazabicyclo[4.5.0]undec-7-ene. However, it is not stated how 3-pentenoates can be obtained from 2-pentenoates.

It is an object of the present invention to provide a process in which 2-pentenoates are converted as completely as possible to 3-pentenoates at relatively low temperatures and in a short time, 4-pentenoates, when present, as far as possible not being converted.

We have found that this object is achieved by a process for the preparation of a 3-pentenoate by isomerization of a 2-pentenoate, wherein a 2-pentenoate is treated with from 0.01 to 0.5 mole of a cyclic, tertiary amine having a $pK_a > 6$ per mole of pentenoate at from 50° to 250° C., and 3-pentenoate is distilled off continuously.

The novel process has the advantages that 2-pentenoates can be substantially converted to 3-pentenoates, the process takes place in a relatively short time and does not require any expensive catalysts, and virtually no isomerization of 4-pentenoates occurs.

The novel process is noteworthy in that Japanese Patent Publication 56-55345 discloses that 3-pentenoates undergo up to 60 mol % isomerization to 2-pentenoates in the presence of 1,8-diazabicyclo[5.4.0]undec-7-ene at 100° C. This is in agreement with the well known fact that conjugated double bonds are thermodynamically favored over isolated double bonds. Also noteworthy is the fact that methyl 2-trans-butenecarboxylate undergoes 61% conversion to methyl 2-cis-butenecarboxylate and only 9% conversion to methyl vinylacetate when treated with 1,8-diazabicyclo[5.4.0]undec-7-ene with continuous distillation of buteneesters at 118°–120° C.

The 2-pentenoates used as starting compounds are preferably derived from alkanols of 1 to 12 carbon atoms, cycloalkanols of 6 to 8 carbon atoms, aralkanols of 7 to 10 carbon atoms, phenols or naphthols. Examples of suitable starting materials are the corresponding methyl, ethyl, n-propyl, isopropyl, tert-butyl, isobutyl, n-butyl, sec-butyl, n-pentyl, n-hexyl, dodecyl, cyclopentyl, cyclohexyl, cyclooctyl, benzyl, phenylethyl and phenyl esters. The 2-pentenoates used as starting materials may be in the cis and/or trans form. Alkyl 2-pentenoates, in particular $C_1$–$C_3$-alkyl 2-pentenoates, are particularly suitable.

The treatment is carried out at from 50° to 250° C., particularly advantageously from 100° to 160° C.

As a rule, the treatment is effected under atmospheric pressure, although it is also possible to employ reduced pressure, for example up to 1 mbar, or slightly superatmospheric pressure, for example up to 10 bar.

The treatment is carried out in the presence of a cyclic, tertiary amine, having a $pK_a$ of $>6$, in particular from 6.2 to 12.

Preferred cyclic, tertiary amines are (a) 5-membered to 7-membered, cyclic, tertiary amines which may contain 1 or 2 nitrogen atoms or 1 nitrogen atom and 1 oxygen atom in the ring, one or both nitrogen atoms being substituted by alkyl of 1 to 4 carbon atoms. Examples of suitable compounds are N-methylpyrrolidine, N-methylpiperidine, N-methylhexamethylene imine, N-ethylmorpholine and N,N'-dimethylpiperazine. 5-membered to 7-membered, tertiary, cyclic amines having only one nitrogen atom in the ring are particularly preferred.

(b) Aminopyridines of the formula I

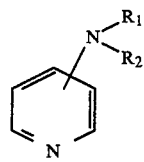

where $R_1$ and $R_2$ are identical or different and are each alkyl of 1 to 4 carbon atoms or, together with the nitrogen atom on which they are substituents, may form a 5-membered to 7-membered ring which may additionally contain an oxygen or nitrogen atom. Particularly preferred compounds of the formula I are those which are derived from 4-aminopyridine. Examples of suitable compounds are N,N-dimethyl-4-aminopyridine, N,N-diethyl-4-aminopyridine, 4-morpholinopyridine and 4-N-piperazinopyridine.

(c) Imidazoles of the formula

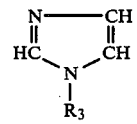

where $R_3$ is alkyl of 1 to 4 carbon atoms. Examples of suitable compounds are N-methyl-, N-ethyl- and N-propylimidazole.

(d) Bicyclic amidines, in particular 1,8-diazabicyclo[5.4.0]undec-7-ene, 1,5-diazabicyclo[4.3.0]non-5-ene and 1,4-diazabicyclo[2.2.2]octane.

It is of course also possible to use mixtures of the abovementioned cyclic, tertiary amines.

From 0.01 to 0.5, in particular from 0.05 to 0.2, mole of cyclic, tertiary amine is used per mole of 2-pentenoate.

The 3-pentenoates formed during the isomerization are distilled off continuously from the reaction mixture, preferably at the rate at which they are formed. For this purpose, the bottom product is heated at the boil, advantageously while continuously feeding in the 2-pentenoate, and the resulting 3-pentenoate is distilled off continuously, preferably at the rate at which it is formed.

It has proven particularly useful to use cyclic tertiary amines which have a boiling point above that of the particular 3-pentenoate formed so that, when 2-pentenoate is fed continuously into the reaction mixture, the cyclic tertiary amine remains behind and only 3-pentenoates are removed from the reaction mixture. If the 3-pentenoate thus obtained also contains residual amounts of 2-pentenoate, the latter can be separated off in a second distillation and are preferably recycled to the isomerization stage.

Compared with the processes known to date, the novel process has the advantage that the 2-pentenoates are converted to 3-pentenoates rapidly, under mild conditions and with high selectivity. Other advantages are the possibility of recovering the nitrogen bases and the fact that the reaction mixtures can be worked up easily. It is also noteworthy that 4-pentenoates present at the same time remain virtually unchanged. This is important since, for example, methyl 2-cis- and 4-pentenoate have virtually the same boiling point and therefore cannot be separated from one another by distillation.

The 3-pentenoates obtainable by the process of the invention are important intermediates for the preparation of adipic acid by hydroesterification.

The Examples which follow illustrate the process according to the invention.

EXAMPLE 1

A mixture of 684 g of methyl 2-trans-pentenoate (boiling point 137° C./1013 mbar) and 73 g of 4-N,N-dimethylaminopyridine was heated to the boil in a 1 distillation flask having an attached packed column (height 2 m, diameter 36 mm, 2.1 of wire coils) and a reflux divider. A pentenoate mixture having a boiling point of 127°–136° C./1013 mbar was taken off at the top of the column (reflux ratio 6:1). Corresponding amounts of methyl 2-trans-pentenoate were metered into the bottom of the column. In the course of 30 hours, 3,936 g of pentenoate mixture were removed from the top of the column, the said mixture consisting of 8% of methyl 2-cis-pentenoate, 14% of methyl 2-trans-pentenoate and 78% of methyl 3-cis- and 3-trans-pentenoate.

EXAMPLE 2

A mixture of 661 g of methyl 2-trans-pentenoate, 68 g of methyl 2-cis-pentenoate and 73 g of 4-N,N-dimethylaminopyridine was heated to the boil in the distillation apparatus described in Example 1. A pentenoate mixture having a boiling point of 125°–134° C./1,013 mbar was taken off at the top of the column (reflux ratio 6:1). Corresponding amounts of a pentenoate mixture consisting of 90% of methyl 2-trans-pentenoate and 10% of methyl 2-cis-pentenoate were metered into the bottom of the column. In the course of 6.5 hours, 704 g of pentenoate mixture were removed from the top of the column, the said mixture consisting of 12% of methyl 2-cis-pentenoate, 12% of methyl 2-trans-pentenoate and 76% of methyl 3-cis- and 3-trans-pentenoate.

EXAMPLE 3

17.1 g of a pentenoate mixture which consisted of methyl 2-cis-pentenoate (20%), methyl 2-trans-pentenoate (40%), methyl 3-cis- and trans-pentenoate (20%) and methyl 4-pentenoate (20%) and 0.95 g of 1,5-diazabicyclo[4.3.0]non-5-ene were heated to 130° C. The mixture of the pentenoates was separated from the catalyst by distillation in a bulb tube apparatus (60°–100° C./20 mbar). Analysis by gas chromatography showed that the distillate (16.5 g) consisted of 2.8% of methyl 2-cis-pentenoate, 48.7% of methyl 2-trans-pentenoate, 27.9% of methyl 3-cis- and trans-pentenoate and 19.9% of methyl 4-pentenoate.

EXAMPLE 4

A mixture of 15 g of methyl 2-cis-pentenoate and 0.2 g of 1,8-diazabicyclo[5.4.0]undec-7-ene was heated to 130° C. After 4 hours, the pentenoate mixture formed was separated from the catalyst by distillation in a bulb tube apparatus. 14.8 g of distillate and 0.3 g of residue were obtained in this procedure. The distillate consisted of 7% of methyl 2-cis-pentenoate, 53.2% of methyl 2-trans-pentenoate and 39.6% of methyl 3-cis- and transpentenoate.

EXAMPLE 5

A mixture of 20 g of methyl 2-cis-pentenoate and 2.1 g of N,N-4-dimethylaminopyridine was heated at 180° C. for 1 hour in a glass autoclave. After this time, analysis by gas chromatography indicated 27.5% of methyl 2-cis-pentenoate, 33.7% of methyl 2-trans-pentenoate and 38.3% of methyl 3-cis- and 3-trans-pentenoate. Methyl 3-pentenoate was then distilled off continuously from the mixture.

EXAMPLE 6

A stirred mixture of 20 g of methyl 2-cis-pentenoate and 2.2 g of 1,5-diazabicyclo[4.3.0]non-5-ene (DBN) was heated at 130° C. for 0.5 hour. After this reaction time, analysis by gas chromatography showed that the reaction mixture consisted of 3.2% of methyl 2-cis-pentenoate, 61.3% of methyl 2-trans-pentenoate and 34.2% of methyl 3-cis- and 3-trans-pentenoate. Methyl 3-pentenoate was then distilled off continuously from the reaction mixture.

When this experiment was repeated under the same conditions with methyl 2-trans-pentenoate, the reaction mixture had the following composition after a reaction time of 0.5 hour: 3.1% of methyl-2-cis-pentenoate, 61.1% of methyl 2-trans-pentenoate and 35.7% of methyl 3-cis- and 3-trans-pentenoate.

EXAMPLE 7

When Example 6 was repeated using 2.7% of 1,8-diazabicyclo[5.4.0]undec-7-ene (DBU) instead of DBN, the reaction mixture had the following composition after 0.5 hour at 130° C.: 3.5% of methyl 2-cis-pentenoate, 63.9% of methyl 2-trans-pentenoate and 32.6% of methyl 3-cis- and trans-pentenoate.

EXAMPLES 8 TO 12

Examples 8 to 12 were carried out in a similar manner to Example 5. The type of pentenoate used, the N base, the reaction time and the composition of the reacted mixture are summarized in Table 1.

| No. | PAE[1] used | Base used | Molar ratio PAE:base | Temp. [°C.] | Reaction time [h] | PGC (% by area, 2-cis- PAE | 2-trans- PAE | 3- PAE |
| --- | --- | --- | --- | --- | --- | --- | --- | --- |
| 8 | 2-cis- | | | | | 52 | 6 | 40 |
| 9 | 2-trans- | DABCO[2] | | 135 | 4 | 2 | 72 | 22 |
| 10 | 2-cis- | | 1:0.1 | 130 | | 79 | 6 | 15 |
| 11 | 2-trans- | DMAP[3] | | 130 | 3 | 1 | 86 | 13 |
| 12 | | | | 180 | | 3 | 52 | 37 |

[1]PAE = methyl pentenoate
[2]DABCO = 1,4-diazabicyclo[2.2.2]octane
[3]DMAP = 4-N,N—dimethylaminopyridine

EXAMPLE 13

A mixture of 22.8 g of methyl 2-trans-pentenoate and 1.7 g of N-methylimidazole was heated at 180° C. for one hour in a glass autoclave. After this time, analysis by gas chromatography indicated 2.0% of methyl 2-cis-pentenoate, 61.5% of methyl 2-trans-pentenoate and 36.3% of methyl 3-cis- and 3-trans-pentenoate. Methyl 3-pentenoate was then distilled off continuously from the reaction mixture.

EXAMPLE 14

A mixture of 22.8 g of methyl 2-trans-pentenoate and 2.0 g of N-methylpiperidine was heated at 180° C. for 4 hours in a glass autoclave. After this time, analysis by gas chromatography indicated 1.2% of methyl 2-cis-pentenoate, 72% of methyl 2-trans-pentenoate and 26.7% of methyl 3-cis- and trans-pentenoate. Methyl 3-pentenoate was then distilled off continuously from the reaction mixture.

COMPARATIVE EXAMPLE 1

A mixture of 11.4 g of methyl 2-cis-pentenoate and 0.79 g of pyridine was heated at 180° C. for 4 hours in a glass autoclave. After this time, analysis by gas chromatography indicated 97% of methyl 2-cis-pentenoate, 0.4% of methyl 2-trans-pentenoate and only 2.5% of methyl 3-cis- and trans-pentenoate.

COMPARATIVE EXAMPLE 2

As described in Example 1, a mixture of 600 g of methyl crotonate (methyl 2-trans-butenecarboxylate, boiling point 118°–120° C./1,013 mbar) and 91 g of 1,8-diazabicyclo[5.4.0]undec-7-ene (BDU) was heated to the boil in a 1 distillation flask having an attached packed column (height 2 m, diameter 36 mm, 2.1 l of wire coils) and a reflux divider. A butenecarboxylate mixture having a boiling point of 108°–112° C./1,103 mbar was taken off from the top of the column (reflux ratio 10:1). Corresponding amounts of methyl crotonate were metered into the bottom of the column. In the course of 37 hours, 615 g of butenecarboxylate mixture were removed from the top of the column, the said mixture consisting of 61% of methyl isocrotonate (methyl 2-cis-butenecarboxylate), 30% of methyl crotonate and only 9% of methyl vinylacetate.

We claim:

1. A process for the preparation of a 3-pentenoate by isomerization of a 2-pentenoate to a 3-pentenoate, wherein the 2-pentenoate is treated with a tertiary amine having a $pK_a$ value $>6$ selected from the group consisting of an aminopyridine of the formula:

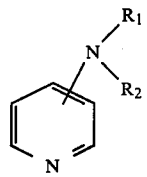

where $R_1$ and $R_2$ are identical or different and are each alkyl of 1 to 4 carbon atoms, or $R_1$ and $R_2$, together with the nitrogen on which they are substituents, may form a 5- of 7-membered ring which may additionally contain an oxygen or nitrogen atom, and an imidazole of the formula:

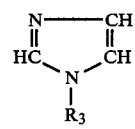

where $R_3$ is alkyl of 1 to 4 carbon atoms.

2. A process as claimed in claim 1, wherein the isomerization is carried out at from 100° to 160° C.

3. A process as claimed in claim 1, wherein from 0.02 to 0.2 mole of tertiary amine is used per mole of 2-pentenoate.

4. The process of claim 1, wherein the tertiary amine is an aminopyridine of the formula:

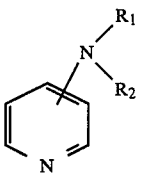

where $R_1$ and $R_2$ are identical or different and are each alkyl of 1 to 4 carbon atoms, or $R_1$ and $R_2$, together with the nitrogen on which they are substituents, may form a 5- or 7-membered ring which may additionally contain an oxygen or nitrogen atom.

5. The process of claim 1, wherein the tertiary amine is an imidazole of the formula:

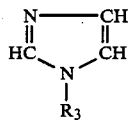

where $R_3$ is alkyl of 1 to 4 carbon atoms.

* * * * *